United States Patent [19]

Dotson

[11] Patent Number: 5,060,062

[45] Date of Patent: Oct. 22, 1991

[54] ELECTRONIC VISION AID DEVICE

[76] Inventor: Robert S. Dotson, 137 Danbury Dr., Oak Ridge, Tenn. 37830

[21] Appl. No.: 517,830

[22] Filed: May 2, 1990

[51] Int. Cl.$^5$ .............................................. H04N 7/00
[52] U.S. Cl. .......................................... 358/94; 358/3; 358/93; 358/88; 351/201; 351/202; 351/158
[58] Field of Search ................... 358/94, 3, 93, 88, 90, 358/91, 92, 108; 351/201, 202, 203, 158

[56] References Cited

U.S. PATENT DOCUMENTS

| | | | |
|---|---|---|---|
| 3,628,193 | 12/1971 | Feinbloom | 358/94 |
| 3,704,378 | 7/1972 | Robb | 358/94 |
| 3,907,434 | 11/1975 | Coles | 358/94 |
| 3,993,407 | 11/1976 | Moricca et al. | 358/94 |
| 3,993,865 | 11/1976 | Bronne et al. | 388/94 |
| 4,227,209 | 10/1980 | Warner | 358/94 |
| 4,516,154 | 5/1985 | Campell | 358/108 |
| 4,516,157 | 5/1985 | Campbell | 358/108 |
| 4,605,959 | 8/1986 | Colbaugh | 358/93 |
| 4,636,866 | 1/1987 | Hattori | 358/88 |
| 4,695,129 | 9/1987 | Faessen et al. | 388/88 |
| 4,743,200 | 5/1988 | Welch et al. | 340/705 |
| 4,802,756 | 2/1989 | Collins | 358/94 |

Primary Examiner—James J. Groody
Assistant Examiner—Michael H. Lee

[57] ABSTRACT

A visual sensory aid system for the partially sighted, designed to be worn around the eyes in a manner similar to that of eyeglasses. Light incident to the image source is detected by receptors mounted on the front lens and processed by the electronic circuitry. The resulting signals, representative of the image, are transmitted to monitor areas on an interior lens that extends from beyond the periphery of one eye to beyond the periphery of the other. The right and left images displayed on the monitor areas are reversed at a high frequency in order to simulate a visual stereo effect for depth perception. Areas of the monitors corresponding to blind spots of the eye are electronically inactivated. A feedback system maintains the focal point of the eye in the optimum direction.

9 Claims, 5 Drawing Sheets

ELECTRONIC VISION AID DEVICE

TECHNICAL FIELD

This invention relates generally to a visual aid for people possessing impaired vision and more especially concerns a system to aid those persons suffering from a specific trauma known as macular degeneration. The system of this invention may take the form of a device to be worn on the head in the place of eyeglasses by such persons, or some other form, such as a screen between a television receiver and the affected viewer, for instance.

BACKGROUND ART

Head-mounted video devices and devices for people with impaired visual acuity are known and patents exist of devices generally related to these fields, of which the following list is a sample.

| PATENT NUMBER | ISSUED TO | DATE OF ISSUE |
| --- | --- | --- |
| 3,993,865 | A. Browne, et al. | November 23, 1976 |
| 4,227,209 | D. A. Warner | October 7, 1980 |
| 4,516,157 | M. G. Campbell | May 7, 1985 |
| 4,605,959 | M. E. Colbaugh | August 12, 1986 |
| 4,636,866 | N. Hattori | January 13, 1987 |
| 4,695,129 | L. Faessen, et al | September 22, 1987 |
| 4,743,200 | B. L. Welch, et al. | May 10, 1988 |

For example, U.S. Pat. No. 4,516,157 for a portable electronic camera, was issued to Malcolm G. Campbell in 1985. However, in contrast to the device of the present invention, this device teaches a system of hands-free camera aiming and is more accurately styled as a device for those having good rather than poor eyesight. His purpose is to enable a wearer to perform hands-free photography.

Similarly, Colbaugh '959, recites a portable communications terminal. His object, also, is to provide hands-free television viewing of a scene, as opposed to being an eyesight aid.

Hattori, '866, and Welch, et al, '200, teach similar, helmet-mounted devices for viewing video images, and the like. Welch teaches the use of fiber optics to achieve a widened angle of view.

Faessen, et al, '129, teaches a head mounted device for viewing cinerama pictures, again relating more to those with good vision rather than being an aid to those with impaired sight. His purpose is to provide a personal viewing, head-mounted screen capable of delivering wide-angle cinerama pictures.

Of the devices known to the inventor which are specifically designed to aid the visually handicapped, Browne, et al, '865, utilizes a hand held scanning device for transmitting printed material to a television screen, making this device, which is not designed to be worn, simply another form of magnification. Warner, '209, is similar to Browne, et al, above, especially in that neither device is designed to be worn by people.

The genesis of the present invention lies in the knowledge that one of the leading causes of blindness in the United States is a group of eye conditions in which the macula (the center part of the retina) is diseased. When this area of the retina is damaged, a person's central or fine vision is destroyed, leaving a large blind spot. As a consequence of such a vision defect, those affected are often effectively blind. They become unable to read, watch television, or even see the face of a loved one. Interestingly, they often retain good peripheral vision.

Heretofore, the only method of helping these persons was to resort to magnifying lenses of various types. Such devices enlarge the image seen by the eye to the point that it is outside, i.e., bigger than, the person's blind spot. Though most of the magnifying devices used have been simple optical lens systems—high plus (convex) lenses or compound lens devices such as binoculars—conventional portable video cameras have been used in combination with macroscopic lenses to enlarge objects sufficiently to be seen by a visually handicapped individual.

All of these various magnification devices have major draw-backs that severely limit their usefulness. High plus lenses, for instance, require very short working distances of only a few inches. Binocular lens systems have very limited fields of view (often less than five degrees). Video reading systems are cumbersome and not very portable.

Today's microelectronics advances make possible some unique devices which can bring new sight to those individuals with macular disease. Various ones of the components which exist because of such advances may be combined into new vision devices which effectively overcome the anatomical deficits that afflict some people.

The device of the present invention combines various pieces of modern video and computer circuitry into an instrument which permits the processing of visual information so as to effectively remove blind spots from a person's field of vision. By modifying the pattern of the incoming light bits which is actually presented to a wearer's eyes, the target visual image is electronically spread apart, both horizontally and vertically (centripetally), thereby leaving a hole in the image corresponding to the macular degeneration blind spot of the wearer.

Accordingly, it is a principal purpose of the present invention to provide a device which enhances the visual perception of persons with impaired vision, preferably by means of electronically detecting and processing minute portions of light which correspond to images, and relaying the reconstructed images to a still-functional area of the eyes of the wearer of the device.

It is another purpose of the present invention to provide such a vision aiding device in a form designed to be worn on the face in the same manner as, and in place of, eyeglasses (spectacles).

DISCLOSURE OF THE INVENTION

A visual sensory aid device for the partially sighted, designed to be worn around the eyes, in the manner of the present style of eyeglasses, supported by the bridge of the nose and the ears. A strap or band can complete the circle around the head, attaching to both ends of the device behind the ears. Light receptor devices are mounted in substantially identical arrays on the front exterior surface (lens), one complete array directly in front of each eye. Light emitting elements, in one embodiment, are mounted in substantially identical arrays on the rear interior surface (lens), one in front of each eye. In another embodiment, a miniature monitor, similar to a CRT, LCD, or the like, instead of an array of individual elements, can be mounted in front of each eye.

Electronic circuitry and a battery operated power supply can be housed in a container attached to a belt or in a pocket and connected to the device by electrical wires or fiber optic cables. In another embodiment, said electronic circuitry can be fitted into the framework of the device as a self-contained unit.

The electronic circuitry scans the light detecting devices and stores in memory the voltage values obtained from each device. The memory values are scanned, in turn, and output to the monitors or light emitting elements. A high-frequency switching circuit can be employed to rapidly reverse the signals sent to each eye so that each eye receives the signal sent to the other eye as well as its own signal many times each second for a stereo effect. A prime feature of the device of the present invention is that individual light (or picture) elements are capable of being selectively left inactivated by the output scanner in order to tailor the transmitted images to exactly fit the blind spot of each eye.

BEST MODE FOR CARRYING OUT THE INVENTION

Figure 1:
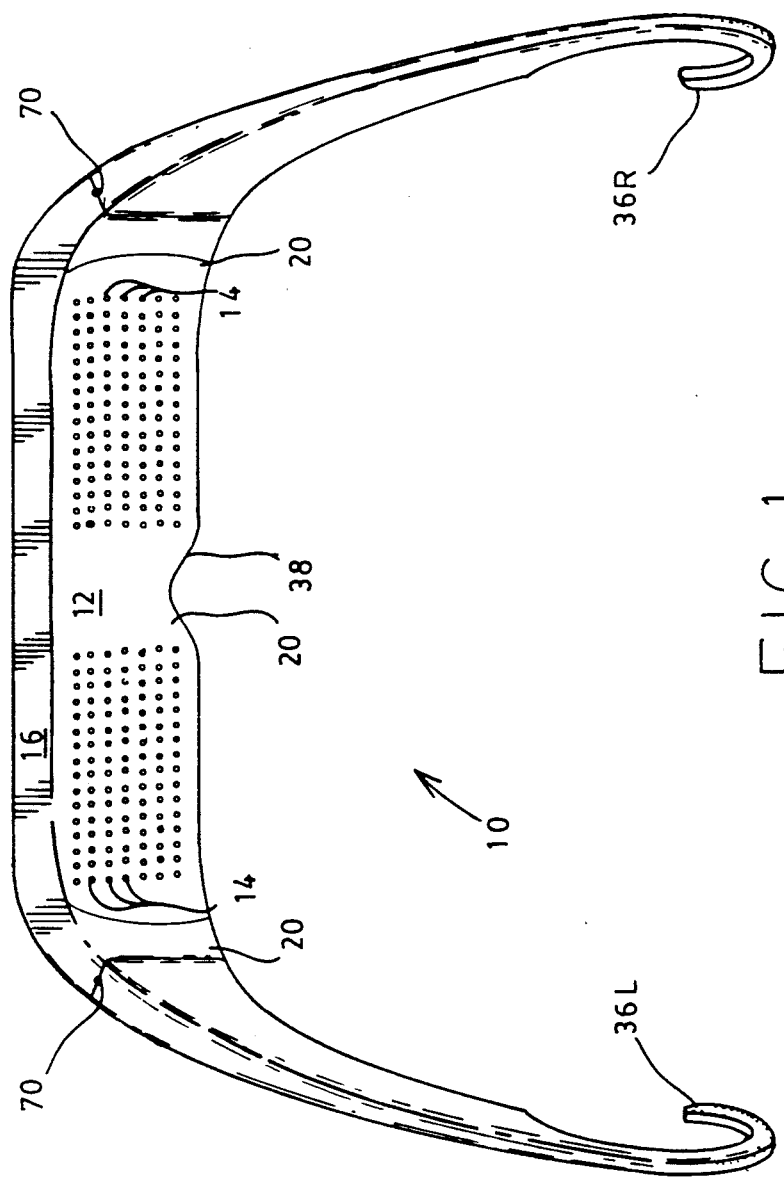
FIG. 1 is a perspective view of a device constructed in accordance with various provisions of the present invention.

A visual sensory aid device for the partially sighted is shown generally at 10 in FIG. 1. In an exemplary embodiment, the device is comprised of a frame 16 which is shaped like an eyeglasses frame, resting upon the nose at the nosepiece 38, and the ears at the earpieces 36R and 36L. A band or cord can be connected between earpieces 36R and 36L to aid in holding the device in place on the head of a wearer. Frame 16 can be of hollow, light-weight material, such as plastic, or the like, to accommodate the routing of wires and the housing of components therein. Hinges 70 can also be provided in one embodiment of the present invention.

Figure 4:
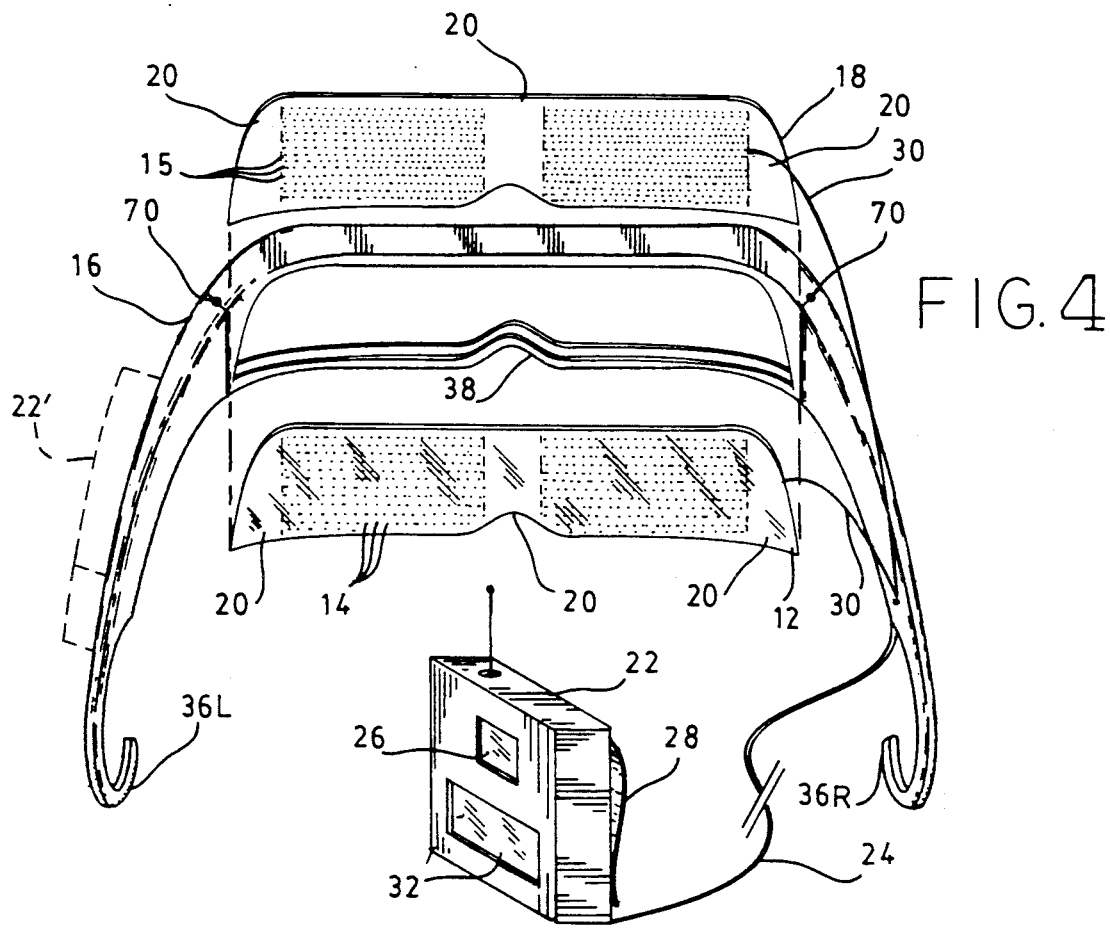
FIG. 4 is an exploded view diagram of a device constructed in accordance with various features of the present invention, showing the interrelationships of the various parts.

As best seen in FIG. 4, frame 16 supports and retains a removable inner lens member 12, and a removable outer lens member 18. A port can be provided for wiring 24 to connect the components in frame 16 to external housing 22, in one embodiment.

Removable exterior lens 18, inserted into frame member 16, is a preferably transparent, semi-rigid material for supporting a plurality of light detecting devices 15 mounted thereon, with the light-sensitive surfaces pointing outward, away from the wearer's eyes. Removable interior lens 12, inserted into frame 16 and compatibly aligned with exterior lens 18, is of similar material and construction as lens 18, except that a plurality of light emitting devices 14 is mounted thereon, with their emitting surfaces facing inward, toward the wearer's eyes.

Removable lenses 12 and 18 can be snapped into grooves in frame 16 in a preferred embodiment. However, it will be seen by those skilled in the art that other methods of mounting light detecting devices 15 and light emitting devices 14 can be employed, and that the exemplary embodiment is simply one illustration.

Figure 5:
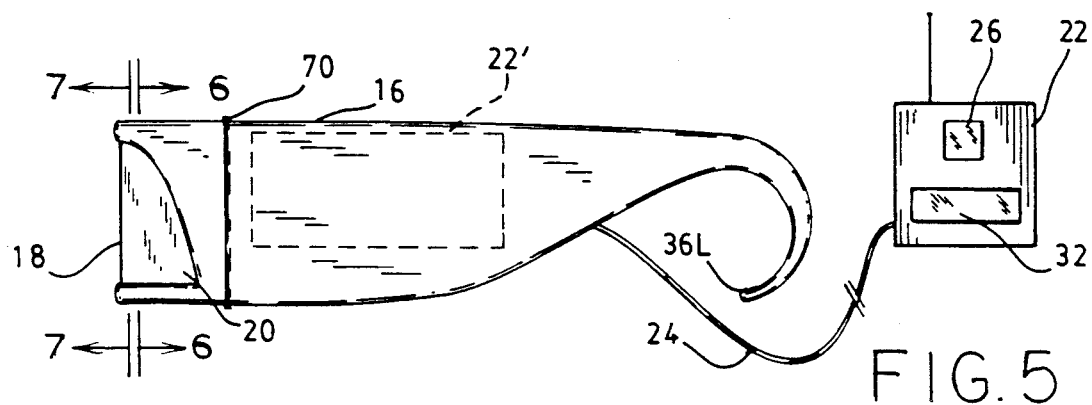
FIG. 5 is a side elevation view of a device constructed in accordance with various features of the present invention.
Figure 6:
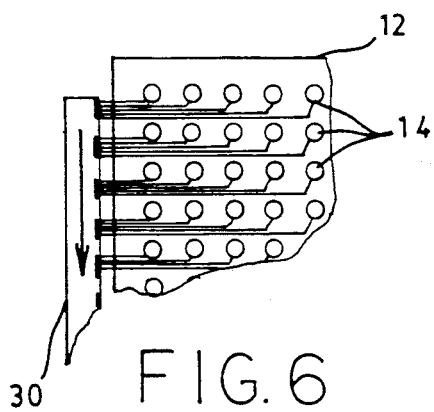
FIG. 6 is a partial cross-sectional view taken at 6—6 of FIG. 5, showing the removable inner lens member.
Figure 7:
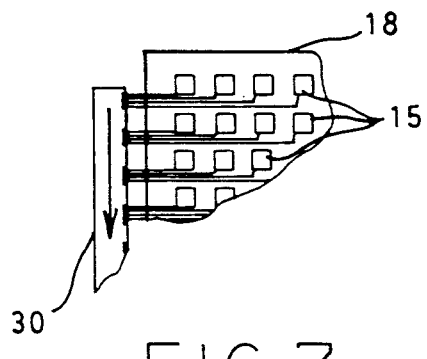
FIG. 7 is a partial cross-sectional view taken at 7—7 of FIG. 5, showing the removable outer lens member.

The electronic components used by the device of the present invention can be mounted in various locations throughout frame 16 as shown in phantom at 22 in FIGS. 4 and 5, or in a separate housing 22 by means of wiring 24, for instance. Housing 22, just as frame 16, can also be of a light-weight material, such as plastic, or the like. Housing 22 can also mount a power on/off switch 26, a belt or pocket clip 28, and a battery compartment cover 32.

The electronic components can be powered by a conventional, state of the art battery power supply 34. The battery can be of any size and shape commensurate with tradeoffs between the power requirements of the electronic circuitry and the weight of the battery required to deliver it.

Exterior lens 18 supports a plurality of light detecting devices 15 mounted thereon, in two 16 row by 16 column arrays, in one embodiment. Of course, it will be seen by those skilled in the art that many other arrangements are possible, and the illustrated embodiment is merely one example. Whatever the size of the arrays, one is disposed directly in front of, and in line with, each eye. Furthermore, other embodiments, such as telescopic or multifocal lens arrays, for instance, are clearly within the scope and intent of the device described herein.

The arrays of light receptor elements 15 on exterior lens 18 are wired to the electronics circuitry by means of connectors 30. In this arrangement, when presented with the light from some object or scene, each detector 15 will receive some light and generate a voltage analogous thereof, representing a minute portion of the overall image. By rapidly and sequentially connecting each detector 15 to an input to the electronic circuit, the overall image casting light on the detectors 15 can be reduced to a series of representative voltage increments.

Figure 3:
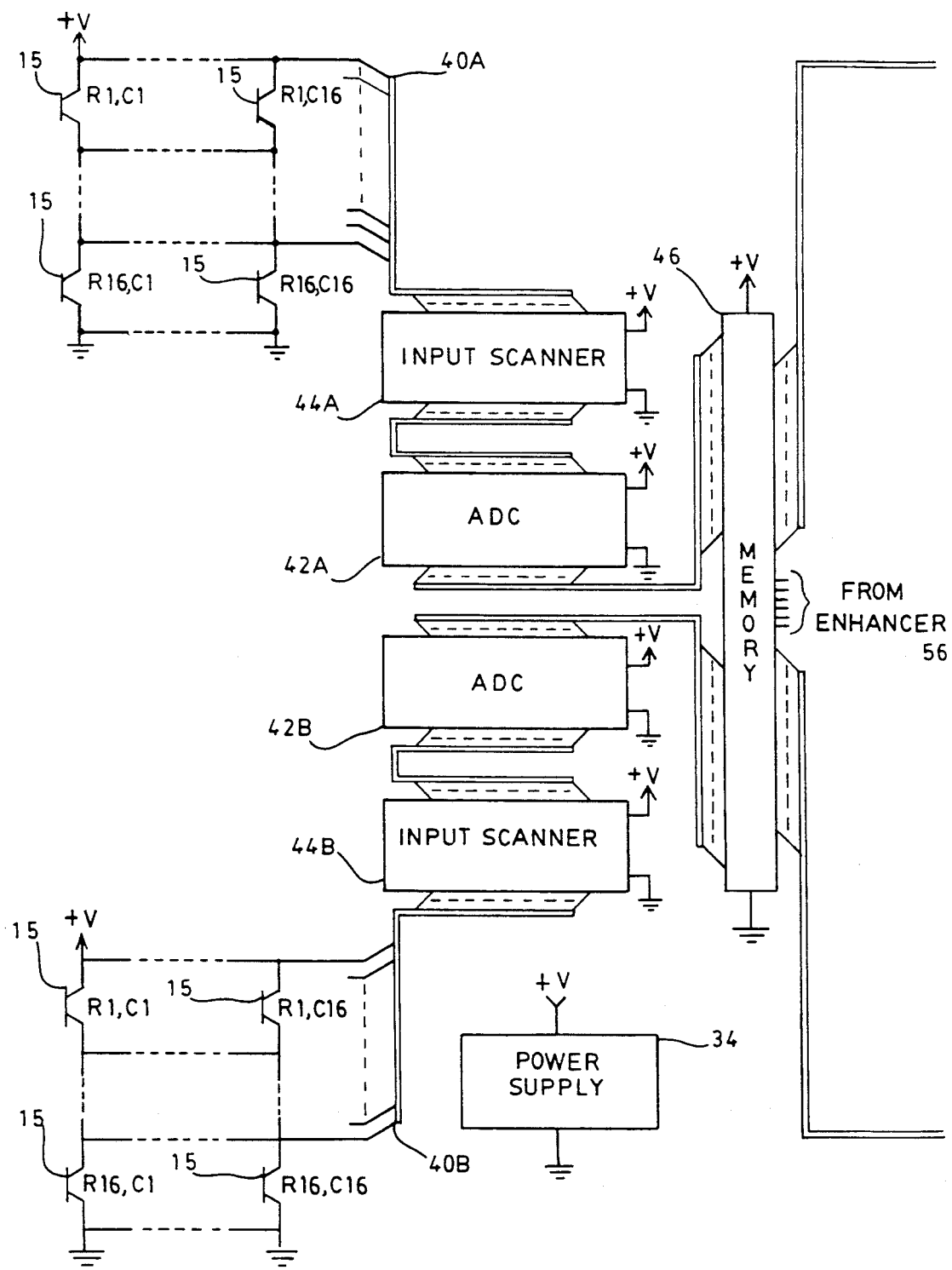
FIG. 3 is a block diagram of the electronic circuitry of a device constructed in accordance with various features of the present invention.
Figure 3:
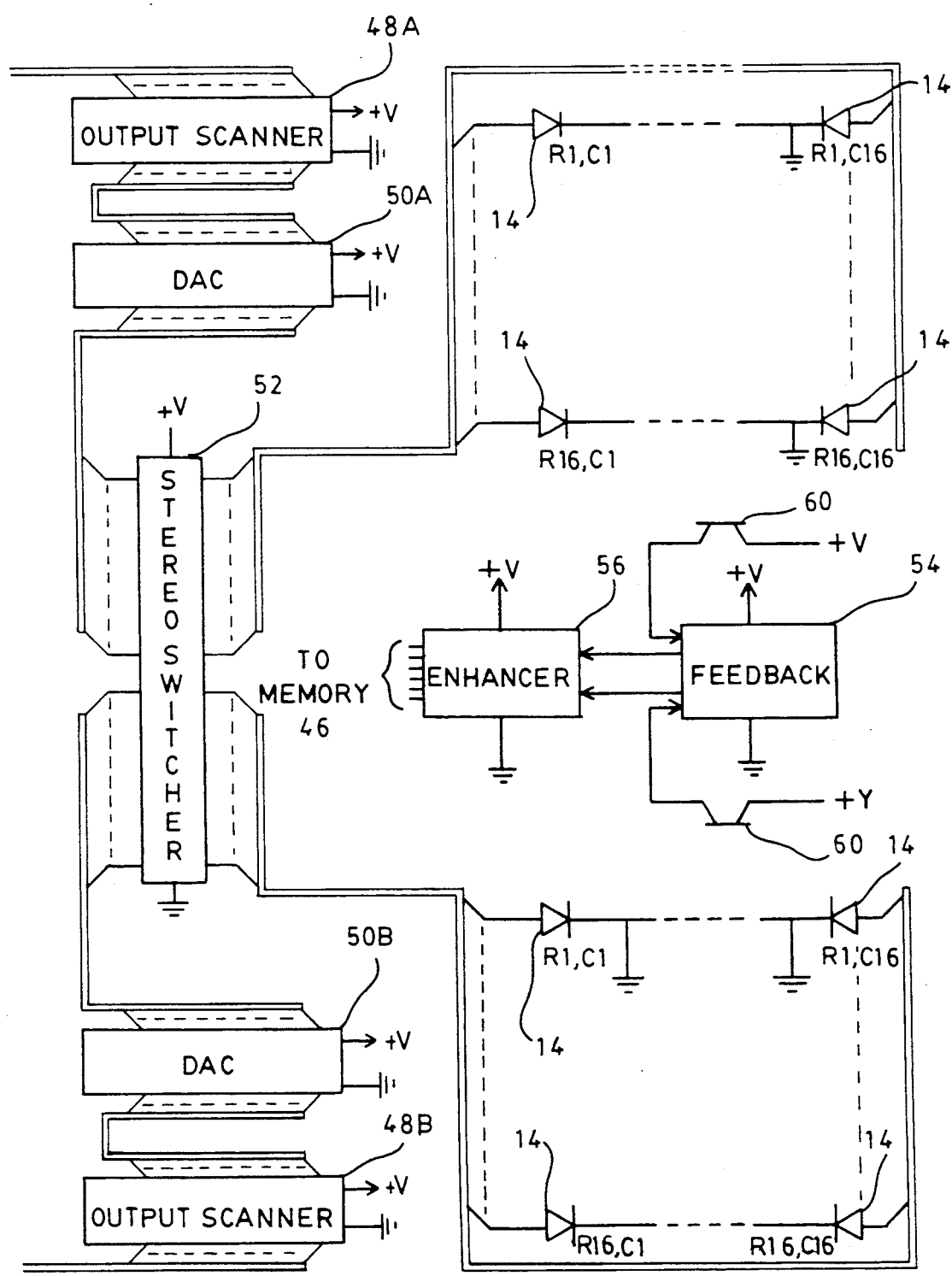

In FIG. 3, it can be seen that these minute increments are input to the electronic circuitry by bus lines 40A and 40B. Buses 40A and 40B conduct each voltage signal from detectors 15 to a separate input of substantially identical microprocessors 44A and 44B, called the input scanners. These input scanners 44A and B sequentially and briefly connect to each input device 15 at a high frequency scanning rate, accepting the analog voltage present on each input device 15 at the time. Scanners 44A and B then send the representative analog voltage signals to a pair of substantially identical Analog to Digital Converters (ADC), 42A and 42B. These ADCs convert the analog voltages to digital values, which are then stored in electronic memory 46, overwriting whatever may have been stored there previously. Thus, the signals in memory are always representative of the latest information being received by the detectors 15.

Each of the signals in memory is then sent to a separate input of substantially identical microprocessors 48A and 48B, called the output scanners. Output scanners 48A and B scan the memory 46 just microseconds after input scanners 40A and B have stored the digital bits therein, transferring said bits to substantially identical Digital to Analog Converters (DAC) 50A and 50B.

In DACs 50A and B, the image signals are converted again, this time from digital values to an enhanced analog version of their original equivalents, which can then be sequentially transmitted to the appropriate light emitting devices 14, following the same scan pattern as input scanners 44A and B.

Various other processes can be applied to the digital and/or analog signals to enhance certain features, such as color, image size, brightness, contrast, etc.

In one embodiment, a high frequency switching circuit 52 can alternate the right and left patterns delivered to each eye, simulating the stereo effect perceived by normal eyes.

A feedback circuit 54 can be employed to ascertain and redirect the focal point of each eye to the optimum location relative to that eye's macular damage pattern. Such a circuit could employ a plurality of light detecting devices 60 to measure light reflected by the retina of the eye to determine the eye's focal direction. The strength of the signals received by detecting devices 60 could be used with an enhancing circuit 56 to enhance selected light emitting devices 14, which would redirect the retina to its optimum location.

A plurality of light emitting devices 14 is mounted on removable interior lens 12, which is inserted into frame member 16 and compatibly aligned with exterior lens 18, each device 14 having its light emitting surface disposed inwardly, toward the wearer's eyes. As output scanners 48A and B send the appropriate signal voltages to each emitting device 14 via connectors 30, each device 14 emits light to the eye of the wearer. As each device is energized, it is seen by the eye as a dot of light of a selected intensity. The speed at which devices 14 are activated provides an apparently cohesive image to the eyes. The cumulative effect of the rapid illumination of each emitting device 14 in sequence, in combination with the natural tendency of the eye to retain an image for a brief period of time after the image has gone, the same characteristic which allows us to see images on a television screen instead of rows of dots, causes the overall pattern of the object(s) detected by detecting devices 15 to be perceived by that peripheral portion of the eye which is still sighted.

However, that portion of the image which would normally be seen by the center of the eye is now seen by the still-sighted periphery of the eye of a wearer of this device and electronically made to appear as though it were in the center.

Figure 2:
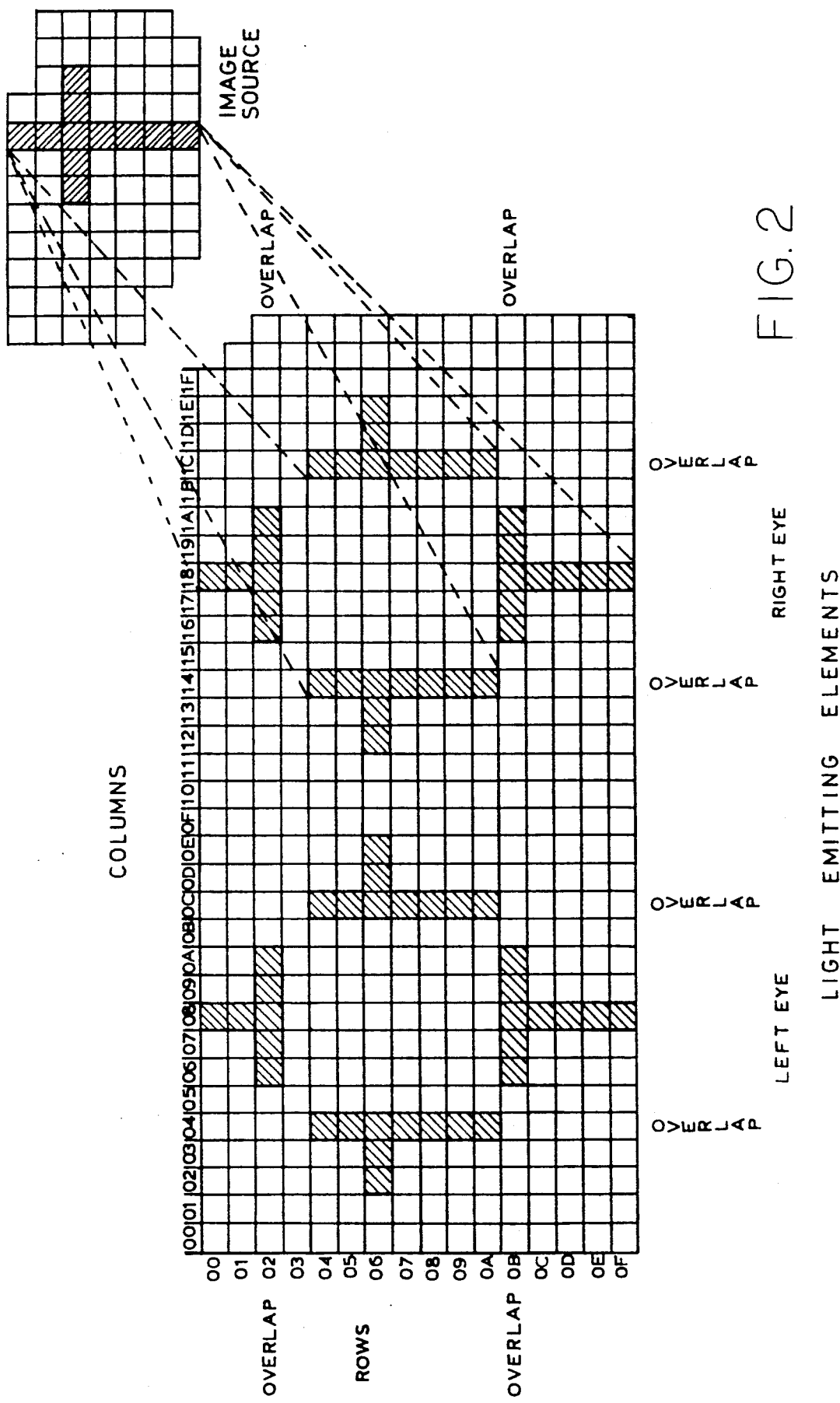
FIG. 2 is a chart of a selected number of the light emitting devices, showing the image transmitted to each eye as the receptors and emitting devices are scanned.

This is done by programming the output scanning microprocessors 48A and B to selectively leave certain emitters 14 inactive, and to transfer signals corresponding to center portions of the image to emitters 14 farther out in the peripheral vision area, shaping a blank area of the overall image created by the emitters 14 to correspond to the blind spot of the eye. Also controlled by instruction codes stored in the microprocessors 48A and 48B is an amount of image overlap around the edges of this blind spot. This principle is illustrated in FIG. 2. The vertical portions are made to overlap horizontally, and the horizontal portions are made to overlap vertically, as illustrated. Actually, the process is effectively the same shape as the eye, rather than simply horizontal or vertical. This overlap effect will tend to bring the edges of the image together in the brain of the wearer to effectively eliminate the blind spot.

From the exploded view in FIG. 4, it can be seen that areas 20 of transparency of lenses 12 and 18 outside the field of detecting devices 15 and emitting devices 14 facilitate the normal usage of extant peripheral vision of the wearer of the device 10 in creating a realistic reproduction of the image being viewed. Portions of the actual image can be seen by the wearer's peripheral vision, with the appropriate portions of the recreated image overlaid thereon. However, in some cases, it may be necessary for lenses 12 and 18 to be opaque.

Of course, it will be seen by those with ordinary skill in the art that the exemplary embodiments described herein are for illustration purposes only and do not limit the present invention to the bounds of such description.

From the foregoing detailed description, it may be seen that a device capable of enhancing the extant sight capabilities of people experiencing macular disfunction has been provided. While a preferred embodiment has been described, it will be understood that there has been no intent to limit the invention to such a disclosure, but rather it is intended that all modifications and alternate constructions falling within the spirit and scope of the invention as defined in the appended claims be covered.

Accordingly, this invention is limited only by the claims appended thereto, and their equivalents, when taken in combination with the complete description contained herein.

We claim:

1. A visual sensory aid system for the partially sighted, comprising:
   a portable imager for wearing on the face in the same manner as, and in place of, eyeglasses;
   electronic circuitry for detecting and processing incident light from an image source into patterns corresponding to said image source, displayed on an inner surface of said sensory aid so as to impinge on those areas of the eyes which still retain sight ability; and
   means for shaping the visual image imparted to conform to the particular shape of the blind spot of each eye of the wearer.

2. The device of claim 1 wherein said imager comprises a light-weight frame in which is removably installed inner and outer lens members for mounting at least one light-emitting device and at least one light-detecting device for each eye.

3. The device of claim 2 wherein said outer lens member contains a plurality of light detecting devices removably installed thereon and said inner lens member contains a plurality of light emitting devices removably installed thereon.

4. The device of claim 2 wherein said outer lens member contains a plurality of light detecting devices removably installed thereon and said inner lens member contains at least one monitor, such as a CRT, LCD, or the like, removably installed thereon.

5. The device of claim 1 wherein said electronic circuitry is contained in a separate housing, remotely located about the body of the wearer from said imager, and connected thereto by conductive means.

6. The device of claim 1 wherein said electronic circuitry is fitted into the frame of said imager, becoming thereby a self-contained unit.

7. The device of claim 1 wherein aid electronic circuitry further comprises a high-frequency switching means for alternating said images between the eyes.

8. The device of claim 1 including means for monitoring the focal position of each eye of a wearer of the device, and means for altering the images fed to said eye so as to realign said focal position to its optimum location.

9. A device for providing to a wearer of said device a selected amount of compensation for a visual disfunction known as macular degeneration, comprising:

a housing for wearing on the face in the same manner as, and in place of, eyeglasses;

an exterior mounting member for mounting a selected number of devices which generate an electrical voltage when impinged upon by light;

an interior mounting member for mounting a selected number of devices which emit light upon application of an electrical voltage thereto;

electronic circuitry for receiving electrical voltage values analogous to light intensity from said voltage generating devices, processing said values in accordance with stored electronic instruction codes, and transmitting new voltage values resultant of said processing to a selected number of said light emitting devices;

means for selectively shaping the pattern of light emitted by a totality of said light emitting devices so as to conform to the shape of the blind spot of each eye of the wearer of the device;

means for selectively altering said light pattern created by said totality of light emitting devices so as to provide a circumferential overlap effect of the actual image as compared to that perceived by the wearer of the device;

feedback means for monitoring the position of the focal point of each eye of the wearer of the device;

means for selectively altering said light pattern so as to redirect said focal point of each eye back to an optimum location; and power supply means for supplying energizing electrical power to said electronic circuit.

* * * * *